United States Patent [19]
Rowland et al.

[11] Patent Number: 5,356,433
[45] Date of Patent: Oct. 18, 1994

[54] BIOCOMPATIBLE METAL SURFACES

[75] Inventors: Stephen M. Rowland, Miami; Kimberly D. Stanley, Florida City, both of Fla.

[73] Assignee: Cordis Corporation, Miami Lakes, Fla.

[21] Appl. No.: 147,017

[22] Filed: Nov. 3, 1993

Related U.S. Application Data

[63] Continuation of Ser. No. 744,537, Aug. 13, 1991, abandoned.

[51] Int. Cl.$^5$ .............. A61F 2/02; A61F 2/06; A61F 2/24; A61F 2/76
[52] U.S. Cl. .................. 623/11; 623/1; 623/900; 623/901; 424/422; 424/423; 427/2.24
[58] Field of Search .......... 424/422, 423; 427/2; 623/1, 11, 900, 901

[56] References Cited

U.S. PATENT DOCUMENTS

| | | | |
|---|---|---|---|
| 3,549,409 | 12/1970 | Dyck | 117/47 |
| 3,585,647 | 6/1971 | Gajewski et al. | 427/2 |
| 3,639,141 | 2/1972 | Dyck | 117/47 A |
| 3,826,678 | 7/1974 | Hoffman et al. | 117/81 |
| 4,378,435 | 3/1983 | Takagi et al. | 435/180 |
| 4,521,564 | 6/1985 | Solomon et al. | 525/54.1 |
| 4,526,714 | 7/1985 | Feijen et al. | 260/112 R |
| 4,539,061 | 9/1985 | Sagiv | 156/278 |
| 4,600,390 | 7/1986 | Gobel et al. | 427/2 X |
| 4,634,762 | 1/1987 | Feijen et al. | 530/350 |
| 4,673,584 | 6/1987 | Nygren et al. | 427/2 |
| 5,030,310 | 7/1991 | Wogoman | 156/252 |
| 5,053,048 | 10/1991 | Pinchuk | 427/2 X |
| 5,112,640 | 5/1992 | Warunek et al. | 427/2 |

FOREIGN PATENT DOCUMENTS

| | | | |
|---|---|---|---|
| 0357003 | 3/1990 | European Pat. Off. | 623/900 |
| 0364787 | 4/1990 | European Pat. Off. | 623/1 |
| 1583008 | 10/1977 | United Kingdom . | |

Primary Examiner—Randall L. Green
Assistant Examiner—Dinh X. Nguyen
Attorney, Agent, or Firm—Lockwood, Alex, Fitzgibbon & Cummings

[57] ABSTRACT

Metallic surfaces of medical devices or components of medical devices are provided that have enhanced biocompatibility properties. The surfaces are prepared by a two-step procedure including covalently linking an organosilane having amine reactive sites with the surface of the metallic member, typically through a metal oxide thereof. Thereafter, a biologically active agent is covalently linked to the organosilane coating. The two-step process is particularly advantageous for preparing medical devices in the form of stents which need to be bent and flexed during implantation procedures.

10 Claims, 7 Drawing Sheets

BIOCOMPATIBLE METAL SURFACES

This application is a continuation of application Ser. No. 744,537, filed Aug. 13, 1991.

BACKGROUND AND DESCRIPTION OF THE INVENTION

The present invention generally relates to metal surfaces of medical devices which are rendered biocompatible, to medical devices including same, to processes for preparing same, and to implanting procedures utilizing same. More specifically, the biocompatible metal surfaces include an amino-functional organosilane which is covalently linked to metal oxides on the metal surface of the device while covalently linking a biologically active agent thereto and thereby to a silane-treated metal surface. This surface has biocompatibility characteristics while simultaneously presenting a surface which encourages endothelialization upon implantation within a blood vessel and the like.

The importance of biocompatibility of surfaces of various medical devices is well-known and has been sought after for many years and through a variety of approaches. Enhanced biocompatibility is needed, of course, when medical devices are to be implanted within a living body for extended time periods including those which are considered to be of a permanent or semi-permanent nature. It is well-known that, generally speaking, biocompatibility properties are enhanced by attempting to secure biologically active agents to surfaces of medical devices, particularly those which contact flowing blood when they are implanted or otherwise used during medical procedures and the like. In many instances, it is particularly undesirable to have the biologically active agent leach away in wet environments such as are encountered by medical devices that engage blood or other body fluids. Many approaches in this area have concentrated on utilizing polymeric surfaces as the surface which encounters the body fluids and then treating those polymeric surfaces according to a variety of procedures. Other approaches have attempted to treat metallic surfaces which are intended to contact body fluids during implantation and the like. Polymeric surfaces and metallic surfaces each pose different problems which must be overcome in order to provide a polymeric or metallic surface that is suitable for implantation and/or extended-time residence within the body.

Generally speaking, the types of treatments which have been implemented or attempted fall into three broad categories. One involves plasma discharge treatments of the medical device surface. Another requires only dipping or similar means for contacting the surface with specific chemical components under treatment conditions (such as elevated temperature) which are less elaborate than plasma discharge treatments. A further treatment type involves chemically oxidizing the metallic surface, such as a tantalum, until enough of a metal oxide layer is provided for bonding.

The present invention avoids the need for plasma discharge treatments while at the same time providing effectively modified metallic surfaces. U.S. Pat. Nos. 3,549,409 and 3,639,141 describe treatments of particular polymeric surfaces by swelling the polymeric surface, bonding an agent thereto and non-covalently coupling heparin to that agent. The latter of these patents mentions contacting the polymeric surface with an amino alkyl trialkoxysilane dissolved in an organic solvent which swells the polymeric material. Another chemical treatment approach is exemplified by U.S. Pat. Nos. 4,526,714 and 4,634,762 which indicate that a surface can be rendered biocompatible by coating it with a conjugate of heparinous material and a protein, with the conjugate being formed by coupling carried out in the presence of 1-ethyl-3-dimethyl-aminopropyl carbodiimide (known as EDC) and the like as a coupling agent. The conjugate is attached to the substrate surface at the sites where the surface free functional groups suitable for binding to the conjugate are present. In order to effect the coupling needed to form this conjugate, these free functional groups on the substrate surface are provided as free amino groups.

Another type of treating procedure which has been suggested and attempted involves treatment of a surface with heparin benzalkonium chloride (known as HBAC). A quaternary amine structure is involved. The result is an ionic linkage, and ionic exchange occurs quite readily. For example, HBAC is easily leached from the treated surface to the extent that substantially all of the heparin is removed within about three days under leaching conditions. In addition, 4M guanidine quickly removes the heparin during a non-physiological test, typically within one hour. Furthermore, because benzalkonium chloride is in essence a surfactant, HBAC is a cytotoxic material as well as a hemolytic material which causes a breakdown of red blood cells.

Other quaternary amine alternatives are believed to be non-hemolytic, for example, tetradodecylammonium chloride (known as TDMAC). These types of materials, which are typically applied from a hydrocarbon solvent system, also provide ionic bonding, and ionic exchange can and does occur quite readily. Because of its molecular structure, heparin and materials having similar functions do not escape quite as readily from TDMAC as for HBAC, but leaching is still very apparent. When attachment to a surface is by means of ionic bonding of TDMAC and the like, most of the heparin or the like is leached away after three hours of contact with blood plasma or after about 24 hours when within a phosphate buffered saline solution under physiological conditions. The ionically attached material is substantially completely removed with guanidine within about one hour during non-physiological testing.

Many of the previous attempts do not fare well under in vivo or biological conditions, and they fall short of fulfilling desirable attributes such as having the coating remain functional for a length of time adequate to provide maximum thrombus prevention. Another particularly important consideration is whether or not the coating interferes with endothelialization. For metallic medical devices which undergo movement such as bending of a portion thereof during implantation and/or use, the mechanical properties of the treatment coating should be able to withstand flexure such as during expansion and the like of the coated member. Exemplary in this regard are metallic radially expandable generally tubularly shaped endoprostheses which are generally known as stents. An exemplary stent in this regard is described in U.S. Pat. No. 5,019,090, the subject matter thereof being incorporated by reference hereinto. Stents such as these are made of very fine gauge metallic wire, typically tantalum wire or stainless steel wire. During implantation, these stents are mounted onto the balloon of an angioplasty catheter or the like until a partially occluded location along a blood vessel or the like is reached, at which time the balloon and the stent are radially and circumferentially expanded for purposes of opening the occlusion and supporting the vessel at that location. This necessarily involves rather extensive bending of the tantalum wire. Many previously available coatings do not have the flexibility and/or adherence properties which are needed to avoid cracking and/or loss of the coating when subjected to this type of flexure.

It is accordingly desirable to be able to utilize a system which meets the objectives of imparting biocompatibility attributes to a metallic substrate so as to substantially prevent thrombus formation on this surface. Furthermore, the system should not crack or otherwise deteriorate due to mechanical movement of the treated metallic member, the system should not allow substantial leaching of the biologically active material, and the system should not substantially interfere with endothelialization after implantation has been completed.

It has been determined that a system providing covalent linkages between a biologically active agent and a metallic surface meets all of these objectives. This includes treatment of the metallic surface of a medical device with an organosilane having amine reactive sites. The organosilane is covalently linked by a condensation reaction with metal oxides of the metallic surface. A biologically active agent such as heparin is applied to the organosilane-coated metallic member, there being a covalent linkage between amine reactive sites of the organosilane and carboxyl moieties or the like of the biologically active agent. Implanting of this device within a blood vessel and the like substantially prevents thrombus formation on the metallic member without significantly interfering with endothelialization of the metallic member. Also, experimental evidence suggests heparin will help modulate smooth muscle cell proliferation associated with re-stenosis or re-occlusion of the dilated vessel.

It is accordingly a general object of the present invention to provide an improved biocompatible metal surface, a method of preparing same, and a method of implanting which utilizes same.

Another object of the present invention is to provide an improved stent or other medical device having a coating treatment which is of a covalent nature and is able to withstand flexure and interaction with fluids.

Another object of this invention is to provide an improved biocompatible metallic surface and method of making same with a covalent linkage between a mucopolysaccharide or a glucose amine and a metallic surface.

Another object of the present invention is to provide an improved implanting method whereby a covalently treated metallic member prevents thrombus formation thereon and does not significantly interfere with endothelialization thereof.

Another object of this invention is to provide an improved metallic stent which is particularly compatible and exhibits advantageous properties conducive of long-term placement within the body.

Another object of the present invention is to provide a stable functionalized metal surface for covalently binding bioactive agents thereto.

Another object of the present invention is to provide a treatment of even fine metal wires without detrimentally affecting the mechanical properties of the metal.

These and other objects, features and advantages of the present invention will be clearly understood through a consideration of the following detailed description.

DESCRIPTION OF THE PARTICULAR EMBODIMENTS

By the present invention, metal surfaces are functionalized by treatment with an amino-functional organosilane in order to provide reaction sites for binding biologically active agents. The invention finds particular application for medical devices having metallic surfaces. Particularly advantageous in this regard are metallic endoprostheses or stents which typically undergo flexure of metallic components. Generally speaking, this flexure occurs when a fine gauge metallic wire or other relatively thin metallic component undergoes bending while the stent moves from a collapsed condition to a radially and circumferentially expanded condition characteristic of implantation within a blood vessel or the like. Typical metallic surfaces include tantalum, stainless steel, platinum-tungsten alloys, and other similar metals and alloys. In addition to expandable stents, the invention finds application in connection with catheter guidewires and other metallic surfaced devices.

Whatever metallic surface is selected, it is first functionalized in order to provide reactive sites. Organosilane materials react with the metallic surface in what is believed to be a condensation reaction between the organosilane and metal oxides of the substrate. A covalent linkage is formed between the metal substrate and the organosilane. A covalent hydrogen bond is believed to be formed.

Amino-terminated organosilanes are of the general formula $NH_2—R—Si—(OR')_n$, wherein R is a lower aliphatic group, R' is H and/or the same or different lower alkyl or phenyl groups, and n is 1, 2 or 3. Preferably, R' is methyl and n is 3. It will be understood that substitution can occur at the amino group when the amino-functional organosilane includes a polymeric or oligomeric backbone, which may itself include repeating amino moieties. Exemplary amino-functional organosilanes include N-(2-aminoethyl-3-aminopropyl)-trimethoxy silane, and 3-aminopropyltrimethoxy silane. An example of an amino-functional polymeric organosilane is N-(trimethoxysilylpropyl)polyethyleneimine, which is a trimethylsilylpropyl substituted polyethyleneimine.

During the condensation reaction by which the amino-functional organosilane is covalently bonded to the metal oxide of the metallic member, it is believed that a reactive silanol group (which may be formed by hydrolysis) condenses with the metal oxide to form the desired covalent bond. When the metal surface being treated is tantalum, a covalent bond is formed between a tantalum oxide layer thereof and the silicon in the silane. This reaction is not ionic, and the silane is substantially permanently bound to the metal oxide, which is incorporated in the crystal lattice structure of the metal and is not easily removable. Chemical means other than ion exchange would have to be employed to remove the silane, and any such chemical means would most likely involve chemical degradation.

Typically, the metallic substrate is dipped into a solution including the silane component, the dipping proceeding for from about 1 to about 10 minutes. Preferably a solvent composed primarily of a lower aliphatic alcohol having a short carbon chain is used as the solvent. For example, a 95% ethanol solution may be used. After dipping has been completed, a curing procedure is followed. Elevated temperature curing is at, for example, about 100° to 120° C. Typically, curing can take between about 5 and about 20 minutes. The result of the condensation reaction is a covalently linked organosilane exhibiting aminofunctionality.

Biologically active agents such as anticoagulants are covalently linked to the coated organosilane. This covalent linkage is typically a condensation or transesterification reaction between the amino-functional groups of the organosilane and carboxyl groups of the biologically active agent. This is a covalent linkage between the organosilane amine group and a carboxylic functionality of the biologically active agent. Usually, this covalent linkage is facilitated by the use of a coupling agent. A well-known coupling agent in this regard is 1,3-ethyldimethyl-aminopropyl carbodiimide, known as EDC. Other typical coupling agents include tertiary butyl isocyanide and Woodward's reagent (N-ethyl-5-phenylisoxazolium 3'-sulfonate) When anticoagulants such as mucopolysaccharides or glucose amines are used, they will typically be applied in aqueous solutions and under acidic conditions. Typically the biologically active agent and coupling agent will be applied as a mixture. For example, ratios of coupling agent such as EDC to biologically active agent such as bovine heparin can be combined and applied at ratios between about 4 to 1 and about 1 to 3. The pH of the applied mixture can be between about 3 and about 3.5. Dipping can proceed for between about 20 minutes and about 1 hour, 20 minutes, typically followed by rinsing and drying in air.

Illustrative biocompatibility agents include anticoagulants or anti-thrombogenic agents such as heparin, hirudin, hyaluronic acid and other mucopolysaccharides or glucose amines. Other biologically active agents such as fibrinolytic, thrombolytic agents, endothelial promoters or smooth muscle cell inhibitors can also be used. These include streptokinase, urokinase, collagen, fibronectin, laminin, growth factors and antibeta fibroblast growth factors. These agents are attached in a manner such that they remain biologically active while at the same time being affixed to the metallic surface in so secure a manner than the agents will not leach away. The biologically active agent is applied from a solution thereof. For example, for procine heparin of 157 units per milligram, the concentration of the solution will be between about 15 and about 25 milligrams per milliliter in water.

An evenly covered biologically active surface is provided onto the metallic surface. This biologically active surface is stable in, for example, phosphate buffered saline solution, at physiological pH values and temperatures. It is also stable in human blood plasma environments, is not a significant cause of hemolysis or cytotoxicity, passes clinical tests for aqueous extracts according to the Italian Pharmacopeia, passes buffering capacity testing according to the U.S. Pharmacopeia, and the coating prevents platelet adhesion and activation. The coating withstands flexure, and the mechanical properties of the metal are not detrimentally affected.

The following examples illustrate the biocompatible anti-thrombogenic coatings for metal surfaces and advantageous properties thereof.

EXAMPLE 1

Figure 1:
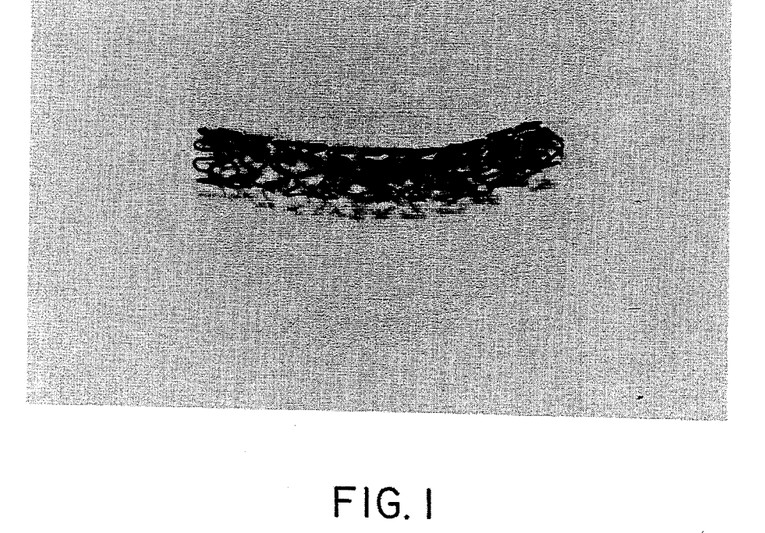
FIGS. 1 and 2 are reproductions of photographs of stents containing a covalent silane-heparin coating.

Stent samples were provided by forming 0.005 inch diameter wire into 6 millimeter coils having an approximate length of 1 centimeter and an estimated surface area of 3.6 square centimeters. Also provided were sample tantalum stents of helically wound tantalum wire having zig-zag undulations as can be seen by FIG. 1. A silane-heparin coating was applied in two steps. First, the stent samples were coated with a solution in 95% ethanol of 2% of an amino-functional silane, N-(2-aminoethyl-3-aminopropyl)trimethoxysilane (available from Petrarch). Each sample stent was dipped into this solution for about 3 minutes. Thereafter, curing proceeded for 10 minutes at 110° C. A bond was formed between the metal and the silane, the bond being understood to be between the tantalum oxide layer on the metal stent samples and the silicon in the silane. The cured samples were next treated with 157 units per milligram of porcine heparin (Hepar). The concentration of the solution was 20 milligrams per milliliter in water, and the pH of the solution was between 3 and 3.5. This heparin solution was mixed with 10 milligrams per milliliter in water of 1,3-ethyldimethyl-aminopropyl carbodiimide (Aldrich) at a pH of 3. The mixture was at a ratio of 3:1 of EDC to heparin, and the dip treatment proceeded for 1 hour. Each sample was rinsed in deionized water and was air dried.

A resulting stent is shown in the FIG. 1 photograph wherein the covalent coating lies closely on the surface of the stent undulations without having coating deposited between the undulations. When this covalent coated stent is expanded, the coating, which conforms exceptionally well to the numerous bends of the stent, does not show evidence of coating cracking but instead bends in conformity with the stent.

EXAMPLE 2

Tantalum sample stents having a configuration as described in Example 1 were treated by a two-step process of applying a silane component and then bonding heparin thereto. Each sample was dipped for about 3 minutes into a solution of silane in 95% ethanol. The solution contained 4% of an aminofunctional polymeric silane, namely trimethylsilylpropyl substituted polyethyleneimine (available from Petrarch). The cure time was 10 minutes at 110° C. to effect the bonding between the tantalum oxide layer on the metal and the silicon in the silane. 157 units per milligram of porcine heparin (Hepar) were used in the next treatment step. The concentration of the solution was 20 milligrams per milliliter in water, and the pH of the solution was between 3 and 3.5. This heparin solution was blended with an EDC solution of 10 milligrams per milliliter in water at a pH of 3, the mixture being at a ratio of 3 to 1 of EDC to heparin. Treatment proceeded for one hour, and the samples were air dried after rinsing in deionized water.

Figure 2:
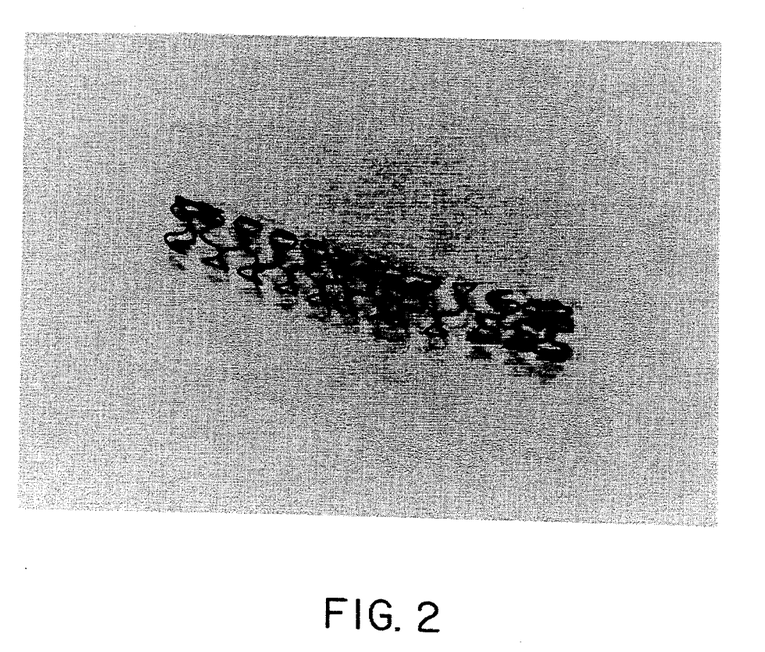

FIG. 2 is a photograph of a stent thus processed, wherein the covalent coating lies closely on the surface of the stent undulations without having coating deposited between the undulations. When this covalent coated stent is expanded, this coating which conforms exceptionally well to the numerous bends of the stent, does not show evidence of coating cracking but instead bends in conformity with the stent.

COMPARATIVE EXAMPLE A

Figure 3:
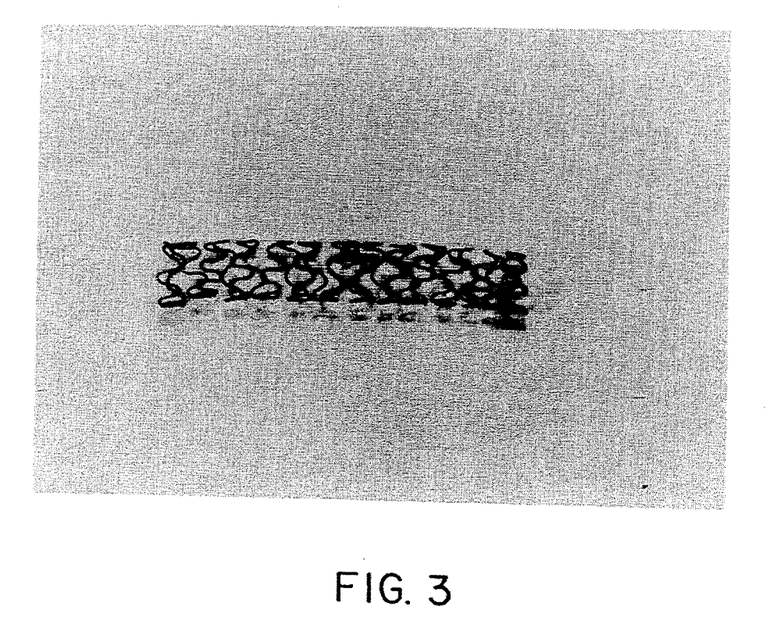
FIGS. 3 and 4 are reproductions of photographs of stents having an ionic heparin coating.

Sample stents as described in Examples 1 and 2 were provided with coatings which are ionic complexes of heparin and tetradodecylmethylammonium chloride (TDMAC). A one-step dip coating process proceeded for about 15 seconds utilizing the ionic complex of heparin and 2% TDMAC. Each sample was air dried under a hood. FIG. 3 is a photograph of one of the stents thus prepared wherein the ionic coating can be seen generally at the bends between the undulations of the stent. When this stent is expanded, cracking of the ionic coating is evident. Each sample stent was packaged individually and sterilized by ethylene oxide sterilization procedures.

COMPARATIVE EXAMPLE B

Figure 4:
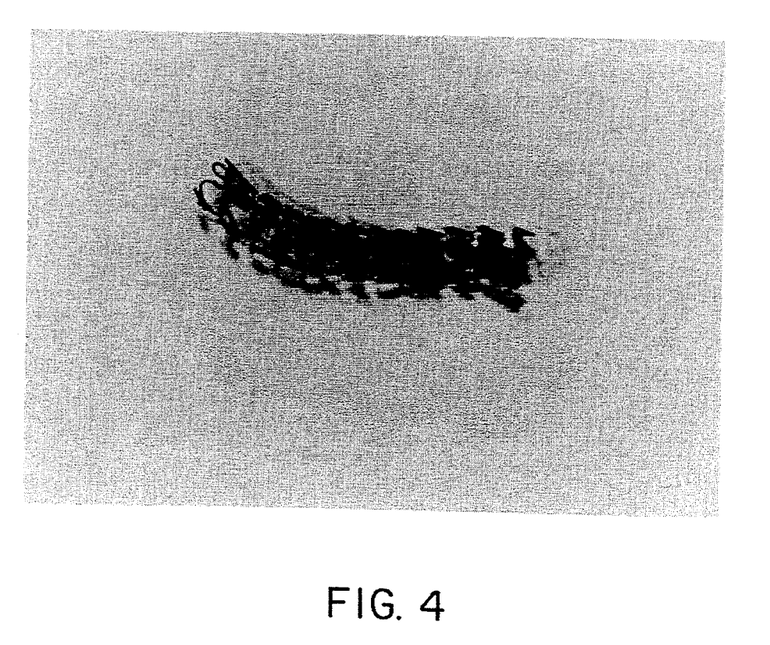

The procedure of Comparative Example A was followed, except a 7% TDMAC solution was used. FIG. 4 is a photograph of a stent thus prepared wherein the ionic coating can be seen generally at the bends between the undulations of the stent. When this stent is expanded, cracking of the ionic coating is evident.

EXAMPLE 3

Five sample stents coated in accordance with each of Examples 1 and 2 and Comparative Examples A and B, together with five control, untreated stent samples were subjected to in vitro testing by subjecting them to phosphate buffered saline extraction procedures. Extractions were carried out in 5 milliliters of phosphate buffered saline (Sigma) at a pH of 7.4 and a temperature of 37° C. Evaluations were made periodically, and the data thus generated are reported in Table I. After these extractions were completed, two samples of each lot were extracted with 4M guanidine hydrochloride (Aldrich) for one hour. A dimethylmethylene blue (Serva) colorimetric assay was performed on each extract. One sample of each was stained with toluidine blue (Fluka) to verify the presence of heparin.

TABLE I

| | EXAMPLE - Colorimetric Assay Concentration (Micrograms/Cm$^2$) | | | | |
|---|---|---|---|---|---|
| TIME | control | Ex. 1 | Ex. 2 | Ex. A | Ex. B |
| 0 min | 0.00 | 0.61 | 2.41 | 6.53 | 23.27 |
| 15 min | 0.00 | 0.41 | 1.17 | 4.59 | 17.74 |
| 30 min | 0.00 | 1.22 | 0.00 | 3.39 | 20.40 |
| 45 min | 0.00 | 3.67 | 0.69 | 12.86 | 17.19 |
| 1 hour | 0.00 | 1.39 | 0.82 | 19.03 | 23.14 |
| 24 hours | 0.00 | 0.00 | 9.09 | 4.62 | 29.62 |
| 48 hours | 0.00 | 1.75 | 3.72 | 10.37 | 3.63 |
| 72 hours | 0.00 | 0.00 | 8.15 | 22.91 | 24.99 |
| 1 week | 0.00 | 0.00 | 0.00 | 33.91 | 49.95 |
| 2 weeks | 0.00 | 0.00 | 0.00 | 11.30 | 30.04 |
| 3 weeks | 0.00 | 0.00 | 0.00 | 69.80 | 68.55 |
| 4 weeks | 0.00 | 0.00 | 0.00 | 85.08 | 88.68 |

The colorimetric assay data of Table I report the concentration in terms of micrograms of heparin leached per square centimeter. None of the covalent silane coated samples of Example 1 showed any significant leaching, and the only leaching which approached significant levels with respect to the covalent silane coated samples of Example 2 were at 24 hours and 72 hours. The two ionic Comparative Examples A and B showed significant leaching in almost all instances, with about 10 or above indicating significant leaching. The data indicate that very little heparin was removed from the coatings including the covalent silane coupling. The staining evidenced that heparin remained on the sample after extraction. The concentration of heparin indicated by the dimethylmethylene blue present on the surface of the samples was very low, being zero in most cases for both Examples i and 2.

Combining these data with the fact that the samples still stained purple after extraction with guanidine for the dimethylmethylene blue indicates that the Example 1 and Example 2 coatings are both covalent coatings, which means that the heparin is permanently attached to the silane coatings. The results indicate that very little heparin actually came off in the phosphate-buffered saline for the Example 1 and Example 2 coatings, even after 4 weeks at 37° C. Furthermore, when the dimethylmethylene blue colorimetric assay was carried out, it was found that the heparin on the Comparative Examples A and B was completely removed by the guanidine. This was verified by staining and comparing the results to those obtained before extraction of the samples for the dimethylmethylene blue colorimetric assay. The complete removal of heparin and the wide range of concentrations indieate an ionic attraction holding the heparin in the coating. These data indicate that, unlike the ionic coatings of Comparative Examples A and B, the covalent coatings of Examples 1 and 2 provide for the presence of bound heparin for a period of time which is long enough to remain until endothialization is substantially completed, which is usually within 2 to 3 weeks after implantation.

EXAMPLE 4

Five samples of each of the stents prepared in accordance with Examples 1 and 2 and Comparative Examples A and B and five controls were each extracted in human blood plasma at 37° C. for either 30 minutes, 1 hour or 3 hours. After the extractions were complete, the plasma was checked for increased clotting time using APTT (Activated Partial Thromboplastin Time) to determine the concentration of heparin present. In addition, the samples were subjected to further testing. Two of each lot were used for dimethylmethylene blue colorimetric dye binding assay, and one of each lot was stained with toluidine blue. The APTT testing showed very little extraction for any of the samples. The dimethylmethylene blue colorimetric analysis and staining showed that the samples all stained purple after extracting with the blood plasma, which indicates that heparin is still present on the surface of the stent. Results of the dimethylmethylene blue colorimetric assay are reported in Table II. The amount of heparin left on each of the Comparative Example A and B stents came off easily using guanidine, while less than significant heparin amounts came off with the 4M guanidine extraction of the Example 1 and 2 stents. The Example 1 and 2 stents still stained purple after the 4M guanidine extraction.

TABLE II

| | EXAMPLE - (Concentration in Micrograms/Cm$^2$) | | | | |
|---|---|---|---|---|---|
| TIME | control | Ex. 1 | Ex. 2 | Ex. A | Ex. B |
| 30 min | 0.00 | 4.18 | 1.53 | 15.31 | 24.28 |

TABLE II-continued

| TIME | EXAMPLE - (Concentration in Micrograms/Cm$^2$) | | | | |
|---|---|---|---|---|---|
| | control | Ex. 1 | Ex. 2 | Ex. A | Ex. B |
| 1 hour | 0.00 | 5.84 | 1.44 | 12.39 | 22.03 |
| 3 hours | 0.00 | 3.09 | 4.61 | 16.83 | 27.09 |

EXAMPLE 5

A flow loop apparatus was used to characterize the interaction of platelets with the stent materials in a flowing situation by passing the calcified blood through a polymethylmethacrylate flow cell apparatus for five minutes in order to obtain information on the biological activity of each coating. This test provides an indication as to blood flow shear rate, which can be important inasmuch as actual shearing both of the coating and of the blood cells themselves may cause complications not sensed by other in vitro testing. Additionally, platelet adhesion and activation is believed to generally mimic that which will be seen under in vivo conditions. Table III and Table IV report the flow loop analysis data, and platelet adhesion information is illustrated in the Scanning Electron Microscopy photographs of FIGS. 5 through 13. The generally round, light-colored dot-like areas are platelets and the light-colored strands or spikes indicate activated platelets. The most advantageous situation is one having the least number of adhered platelets which are activated.

Figure 5:
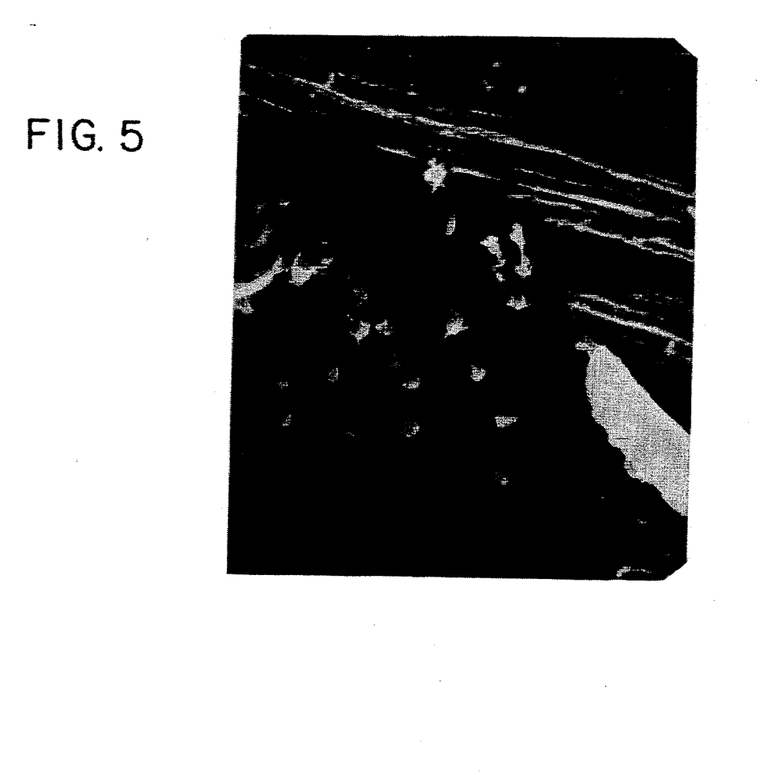
FIG. 5 is an SEM photograph of an uncoated stent that had been subjected to flow loop analysis as described in Example 5 hereof.
Figure 6:
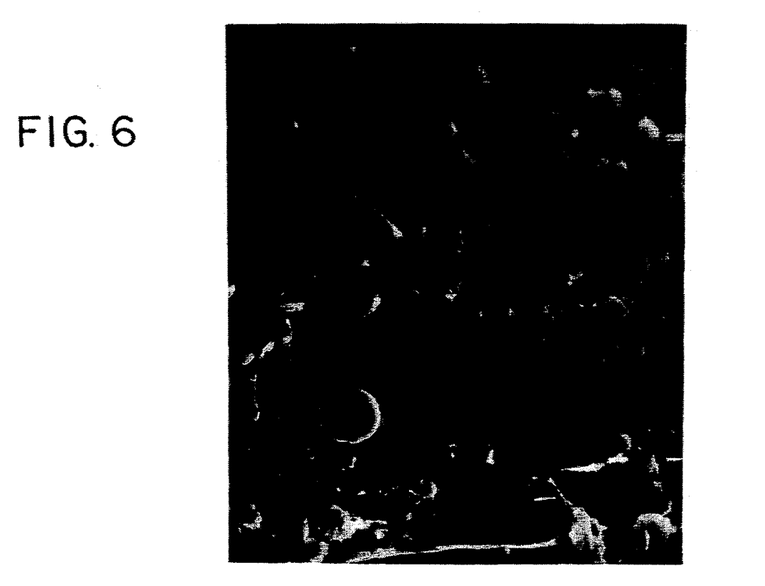
FIGS. 6, 7, 8 and 9 are SEM photographs of ionic heparin coated stents that had been subjected to flow loop analysis in accordance with Example 5.
Figure 7:
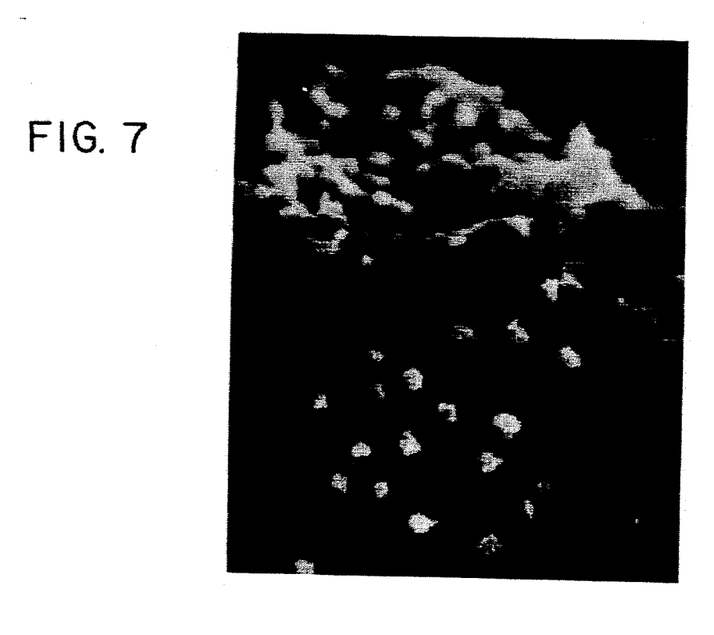
Figure 8:
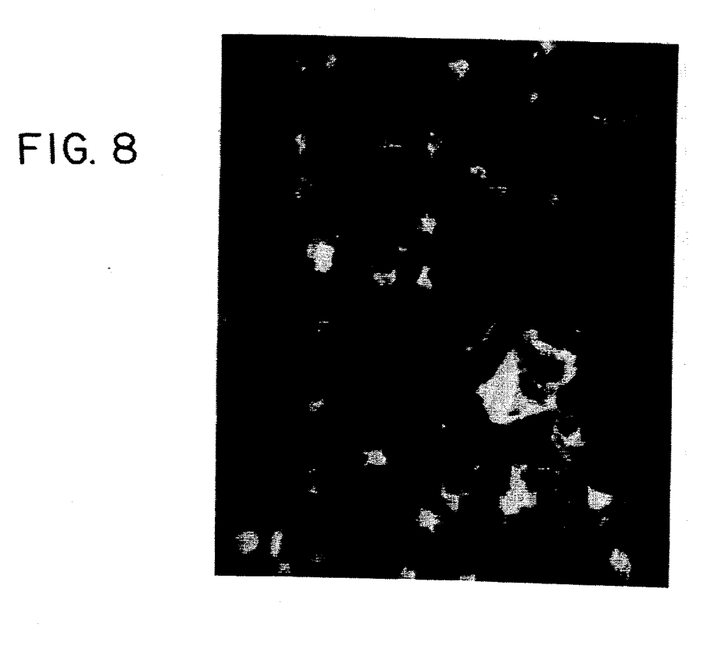
Figure 9:
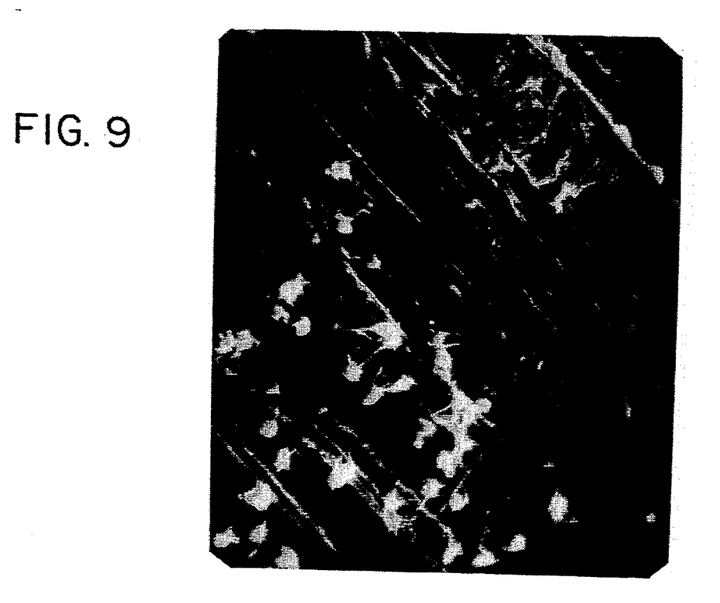
Figure 10:
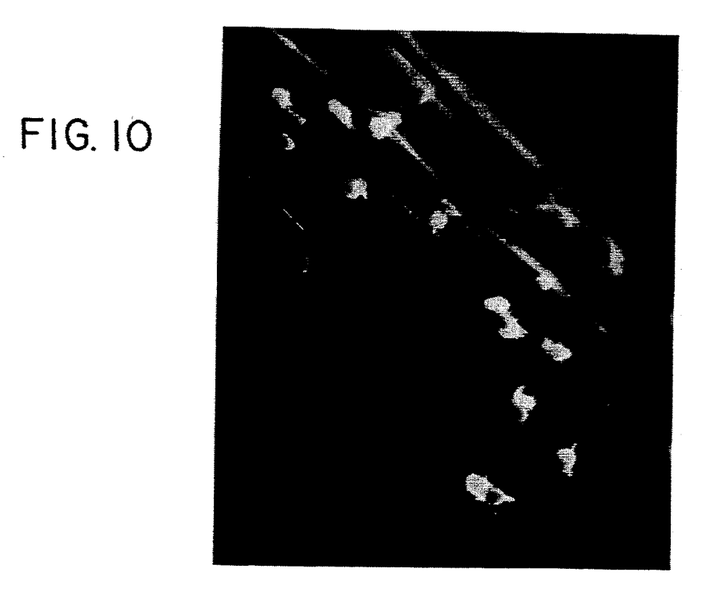
FIGS. 10, 11, 12 and 13 are SEM photographs of covalent silane-heparin coated stents which had been subjected to flow loop analysis as described in Example 5.
Figure 11:
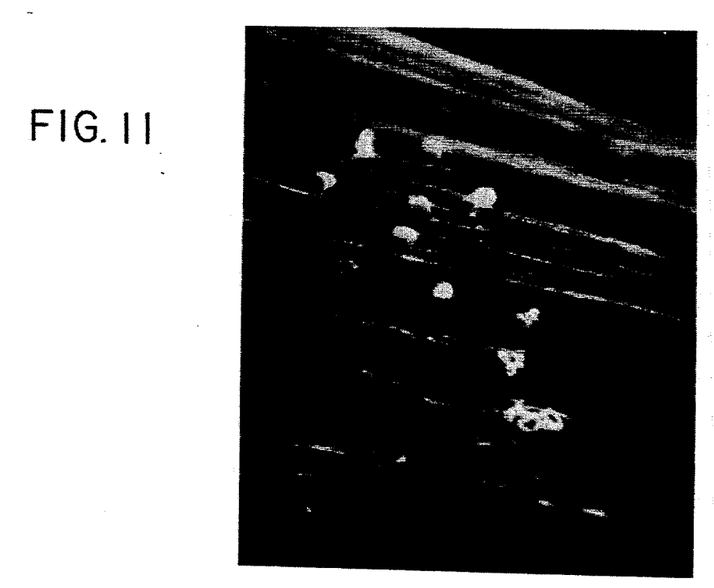
Figure 12:
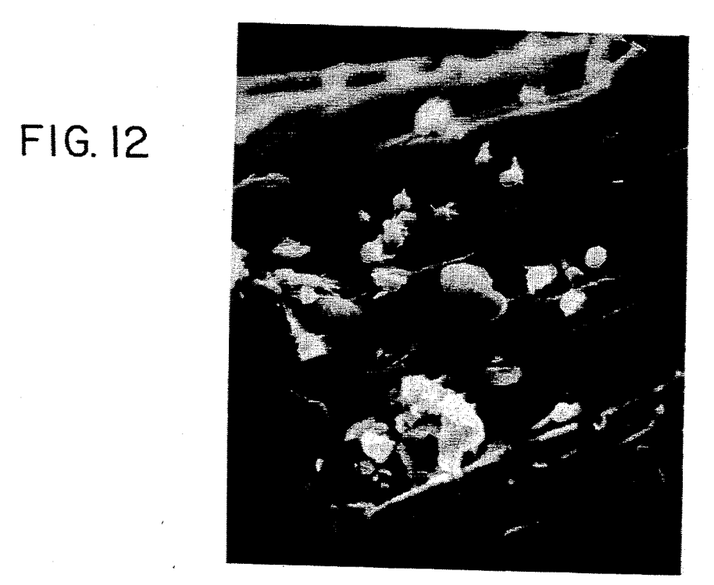
Figure 13:
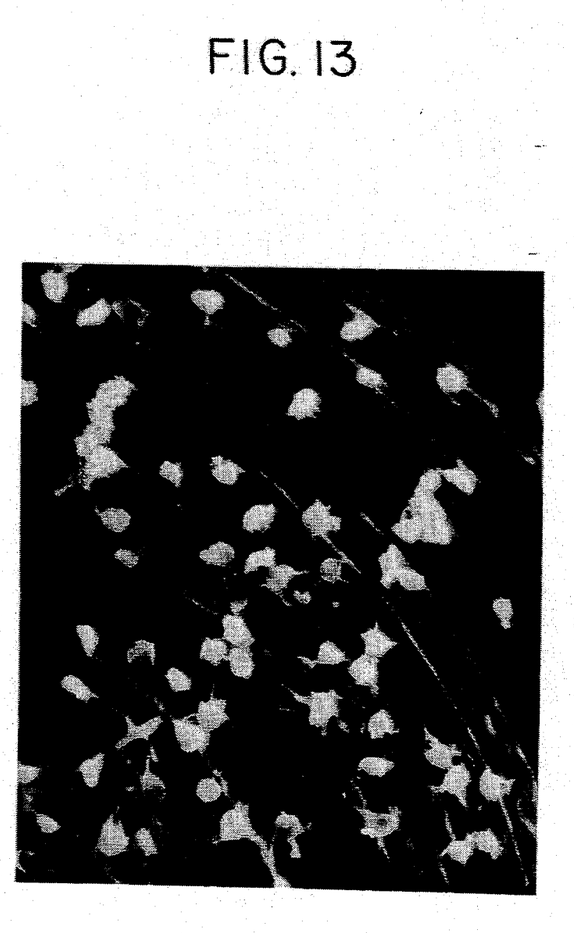

FIG. 5 represents the uncoated controls. FIGS. 6 and 7 show a large number of platelets adherring to the Comparative Example A samples, most of which are highly activated with pseudopods extending. FIGS. 8 and 9 show a moderate amount of platelets adherring to the Comparative Example B samples, these platelets too being activated, although not to the extent seen in the comparative Example A samples. The Example 2 samples of FIGS. 12 and 13 show a great deal of debris from the blood adherring to the surface of the sample. Additionally, there are a large number of platelets attached to the surface of the stent, these platelets being in the highest stage of activation, showing a great deal of aggregation. In addition to the high activation of the platelets, a very high percentage of hemolysis occurred when the blood contacted these samples in this flowing environment. The Example 1 samples of FIGS. 10 and 11 show very little platelet adhesion. In addition, the platelets that did adhere were only slightly activated, most remaining slightly spherical in shape with only a small indication of pseudopods developing. The control samples exhibited a moderate amount of platelet adhesion, with the platelets showing signs of activation.

TABLE III

| Sample | APTT | Hb | PKK | Platelet Aggregation |
|---|---|---|---|---|
| Control | no change | 23% I | 28% I | 40% D |
| Control | no change | 62% I | — | 100% D |
| Ex. A uncleaned | no change | 32% I | 200% I | 17% D |
| Ex. A | no change | 18% I | 11% I | 30% D |
| Ex. B uncleaned | no change | 42% I | 4% I | — |
| Ex. B | no change | 8% I | 8% I | 34% D |
| Ex. 1 uncleaned | no change | 3% I | 14% I | 64% D |
| Ex. 1 | no change | 10% I | 208% I | 45% D |
| Ex. 2 uncleaned | no change | 240% I | 15% I | 10% I |

TABLE III-continued

| Sample | APTT | Hb | PKK | Platelet Aggregation |
|---|---|---|---|---|
| Ex. 2 | no change | 79% I | 10% I | 19% D |

In Table III, APTT indicates whether or not heparin was released. Hb refers to hemoglobin, and this column shows the percentage increase of hemoglobin released into the plasma after contact with the stent, thereby providing an indication of hemolysis. The "I" indicates an increase, and the "D" indicates a decrease. PKK designates Preallikrein, and this column reports the detected percentage increase of activation of Preallikrein due to contact of the stent with the blood in order to thereby provide a measurement of biocompatibility. The platelet aggregation column shows a percentage increase or decrease of platelet reactivity to ADP following contact with the sample. The aggregation of platelets is affected by interaction between the coated samples and the platelets within the flow loop.

TABLE IV

| Sample | Platelets | S.D. | Range | Area (mm$^2$) |
|---|---|---|---|---|
| Control | 94 | 32 | 62–126 | 6.7 × 10$^{-3}$ |
| Catheter | 82 | 17 | 75–99 | 2.3 × 10$^{-3}$ |
| Control | 94 | 32 | 62–126 | 6.7 × 10$^{-3}$ |
| Catheter | 38 | 15 | 23–53 | 2.3 × 10$^{-3}$ |
| Ex. 2 uncleaned | 36 | 16 | 20–52 | 6.7 × 10$^{-3}$ |
| Catheter | 42 | 21 | 21–63 | 2.3 × 10$^{-3}$ |
| Ex. 2 | 80 | 38 | 42–118 | 6.7 × 10$^{-3}$ |
| Catheter | 84 | 17 | 67–101 | 2.3 × 10$^{-3}$ |
| Ex. A uncleaned | 66 | 39 | 27–105 | 6.7 × 10$^{-3}$ |
| Catheter | 44 | 7 | 37–51 | 2.3 × 10$^{-3}$ |
| Ex. A | 56 | 31 | 25–87 | 6.7 × 10$^{-3}$ |
| Catheter | 53 | 34 | 19–87 | 2.3 × 10$^{-3}$ |
| Ex. B uncleaned | 40 | 41 | −1–81 | 6.7 × 10$^{-3}$ |
| Catheter | 36 | 33 | 3–69 | 2.3 × 10$^{-3}$ |
| Ex. B | 37 | 29 | 8–66 | 6.7 × 10$^{-3}$ |
| Catheter | 54 | 30 | 24–84 | 2.3 × 10$^{-3}$ |
| Ex. 1 uncleaned | 11 | 9 | 2–20 | 6.7 × 10$^{-3}$ |
| Catheter | 49 | 43 | 6–92 | 2.3 × 10$^{-3}$ |
| Ex. 1 | 20 | 21 | −1–41 | 6.7 × 10$^{-3}$ |
| Catheter | 49 | 43 | 6–92 | 2.3 × 10$^{-3}$ |

In Table IV, "catheter" refers to the data collected in connection with the catheters upon which the stent was mounted during this flow loop platelet count analysis. The "Platelets" data report a mean of six fields including three on the curve and three straight segments. Generally speaking, a higher number of platelets indicates undesirable increased platelet activation.

EXAMPLE 6

Stainless steel catheter guidewires were coated in two steps. An amino terminated organosilane was applied from a 95% ethanol solution containing 2% of the silane. Each sample was dipped for about 5 minutes, followed by curing for 10 minutes at 110° C. After curing was completed, each sample was treated with 157 units per milligram of porcine heparin (Hepar), the concentration of solution being 20 milligrams per milliliter in water. The pH of this solution was between 3 and 3.5. The heparin was blended with 1,3-ethyldimethylaminopropyl carbodiimide at a ratio of 3 to 1 of EDC to heparin. The EDC solution was at 10 milligrams per milliliter in water at a pH of 3. The time of treatment with the EDC-heparin blend was 30 minutes.

The samples were air dried after rinsing in deionized water.

EXAMPLE 7

Platinum-tungsten alloy wire was subjected to the two-step treatment. Each wire was first dipped in a 2% solution of aminopropyltrimethoxysilane for five minutes. Each sample was briefly dried before curing in an oven, the oven cure being for 10 minutes at 110° C. After cooling, the samples were heparinized with a solution that contained 20 milligrams per milliliter of heparin and 10 milligrams per milliliter of 1,3-ethyl-dimethylaminopropyl carbodiimide in a 2 to 1 ratio of EDC to heparin. Both solutions were at a pH of 3 prior to mixing. The heparinization reaction proceeded for 30 minutes. The reaction having been completed, the samples were rinsed and then allowed to air dry.

It will be understood that the embodiments of the present invention which have been described are illustrative of some of the applications of the principles of the present invention. Numerous modifications may be made by those skilled in the art without departing from the true spirit and scope of the invention.

We claim:

1. A medical device having a biocompatible surface, the biocompatible surface having been made by a process comprising the steps of:
   providing a metallic member having a tantalum oxide-containing surface thereof, said metallic member being flexible and being sized and shaped as a stent;
   treating the tantalum oxide containing surface with an amino-terminated organosilane having amine reactive sites and covalently linking the organosilane with the flexible metallic member to effect a condensation reaction that covalently links the tantalum oxide and silicon moieties of the organosilane in order to form a flexible organosilane-coated tantalum stent;
   applying a biologically active agent compostion to the organosilane-coated tantalum stent and forming a covalent linkage between the organosilane and the biologically active agent to provide a coated flexible tantalum stent; and
   the coated flexible tantalum stent thus formed has a coating which withstands cracking upon flexure, and the tantalum stent thus formed is a biocompatible tantalum stent which, when implanted within a living body, prevents substantial thrombus from occurring on its surface while not significantly interfering with endothelialization of said surface.

2. The medical device in accordance with claim 1, wherein the covalent linkage of the applying and forming step is between the amine moiety of the amino-terminated organosilane and a carboxyl moiety of the biologically active agent.

3. The medical device in accordance with claim 1, wherein said step of treating and covalently linking includes dipping the metallic member into an organosilane of the formula $NH_2-R-Si-(OR')_n$, wherein R is a short chain length aliphatic group, R' is selected from the group consisting of methyl and ethyl, and n is 3.

4. The medical device in accordance with claim 1, further including curing the organosilane-coated metallic member at an elevated temperature prior to said step of applying and forming.

5. The medical device in accordance with claim 1, wherein said flexible metallic member has a generally helical configuration.

6. The medical device in accordance with claim 1, wherein said flexible metallic member is a generally helically wound tantalum stent.

7. A medical device having a biocompatible antithrombogenic tantalum surface, comprising:
   a metallic member for a medical device, the metallic member having a tantalum oxide surface and being flexible and being sized and shaped as a stent, the metallic member having a biologically active surface treatment covalently adhered to the tantalum oxide surface;
   said biologically active surface treatment including an organosilane component having amine reactive sites, the organosilane component having silicon moieties covalently linked to tantalum oxide moieties of the metallic member, said biologically active surface treatment further including a biologically active agent covalently bound to the organosilane component to define a biocompatible tantalum stent; and
   said biocompatible tantalum stent has a surface which substantially prevents thrombus formation thereonto while avoiding any significant interference of the development of endothelialization of the biocompatible tantalum stent, and said biocompatible tantalum stent has a coating which is flexible and which withstands cracking upon flexure.

8. The medical device in accordance with claim 7, wherein said flexible metallic member has a generally helical configuration.

9. The medical device in accordance with claim 7, wherein the metallic member is a generally helically wound tantalum stent.

10. The medical device in accordance with claim 9, wherein said organosilane component is of the formula $NH_2-R-Si(OR')_3$, wherein R is a short chain length aliphatic group and R' is selected from the group consisting of methyl and ethyl, and said biologically active agent is selected from the group consisting of a mucopolysaccharide and a glucose amine.

* * * * *

UNITED STATES PATENT AND TRADEMARK OFFICE
CERTIFICATE OF CORRECTION

PATENT NO. : 5,356,433
DATED : October 18, 1994
INVENTOR(S) : Stephen M. Rowland and Kimberly D. Stanley It is certified that error appears in the above-indentified patent and that said Letters Patent is hereby corrected as shown below:

Col. 2, line 48, "in vivo" should be in italics.
Col. 3, line 63, "binding" should read --bonding--.
Col. 5, line 59, "than" should read --that--; line 61, "procine" should read --porcine--.
Col. 7, line 37, "in vitro" should be in italics; in Table I, under "Ex. B" at 48 hours, "3.63" should read --23.63--.
Col. 8, line 12, "Examples i and 2" should read --Examples 1 and 2--.
Col. 9, line 20, "in vitro" should be in italics; line 22, "in vivo" should be in italics.
Col. 10, line 62, "of solution" should read --of the solution--.

Signed and Sealed this

Twelfth Day of December, 1995

Attest:

BRUCE LEHMAN

Attesting Officer

Commissioner of Patents and Trademarks